United States Patent [19]

Gray et al.

[11] 4,228,035
[45] Oct. 14, 1980

[54] IRRADIATED POLYMER SUPPORTED METAL CATALYST

[75] Inventors: Harry B. Gray, Pasadena, Calif.; Claude C. Frazier, Memphis, Tenn.

[73] Assignee: California Institute of Technology, Pasadena, Calif.

[21] Appl. No.: 682,520

[22] Filed: May 3, 1976

[51] Int. Cl.³ .............................................. C08F 31/22
[52] U.S. Cl. ........................... 252/431 R; 252/431 C; 252/431 N; 252/431 P; 585/275; 585/377; 585/378
[58] Field of Search ............ 252/431 N, 431 P, 431 R, 252/431 C

[56] References Cited

U.S. PATENT DOCUMENTS

| 2,861,045 | 11/1958 | Langer | 252/431 P X |
|---|---|---|---|
| 3,652,678 | 3/1972 | Allum et al. | 252/431 P X |
| 3,674,768 | 7/1972 | Allum et al. | 252/431 P X |
| 3,681,021 | 8/1972 | Mikovsky et al. | 252/431 P X |
| 3,725,306 | 4/1973 | Yoo | 252/431 P X |
| 3,793,354 | 2/1974 | Schwager et al. | 252/431 N X |
| 3,847,997 | 11/1974 | Allen | 252/431 P X |
| 3,872,026 | 3/1975 | Dunn | 252/431 P X |
| 3,900,557 | 8/1975 | Strathdee | 252/431 P X |

OTHER PUBLICATIONS

Lapporte et al., J. Org. Chem. 28 (Jul. 1963), pp. 1947-1948.

*Primary Examiner*—Patrick Garvin
*Attorney, Agent, or Firm*—Poms, Smith, Lande & Rose

[57] ABSTRACT

Novel polymer supported catalysts are prepared by irradiation of low valent transition metal compounds such as iron carbonyl in the presence of solid polymers containing ligands such as phosphinated polystyrene. Hydrogenation of olefins at ambient conditions has been demonstrated.

5 Claims, 1 Drawing Figure

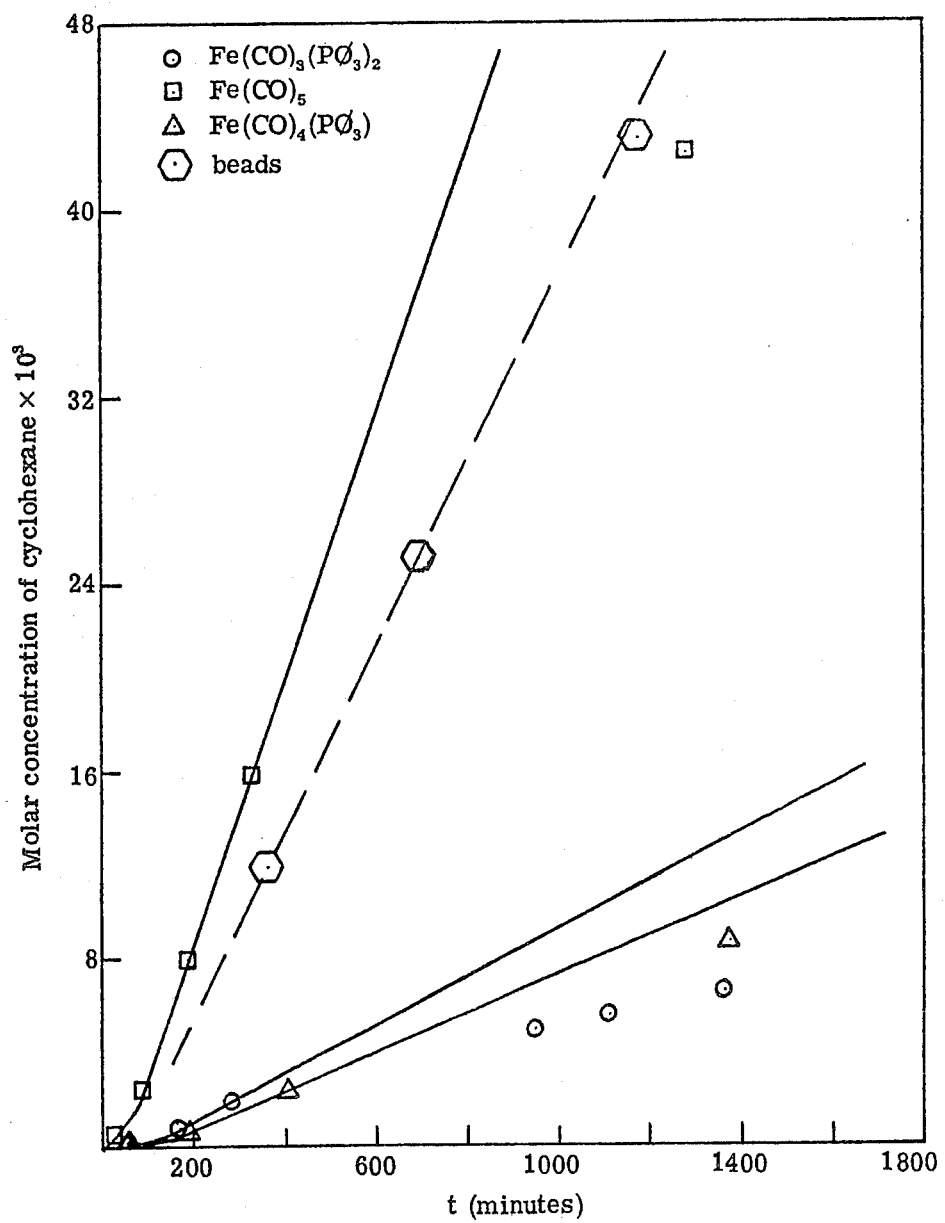

IRRADIATED POLYMER SUPPORTED METAL CATALYST

BACKGROUND OF THE INVENTION

1. Field of the Invention

The present invention relates to polymer supported transition metal catalysts and more particularly to the preparation of these catalysts by photochemical addition of the transition metal compound to the polymer support and to the use of the catalysts in chemical reactions under mild conditions.

2. Description of the Prior Art

The relative merits of homogeneous and heterogeneous catalysts are well known. Homogeneous catalysts have better defined active sites, usually have all of the metal available for catalysis, and offer steric and electronic environments of the metal atom that can, at least in principle, be varied at will. The major disadvantage of homogeneous catalysts is the need to separate them from reaction products without loss of their valuable metal content. This step can be both complex and expensive. Other disadvantages are that these catalysts are relatively easily deactivated through aggregation or by poisonous by-products or at extreme temperatures. Also, corrosion of reactors by metal complexes is common.

In the last few years many advances have been made in transition metal homogeneous catalysis. Efficient transition metal catalysts are known for a variety of useful reactions, such as the reduction of unsaturated organic molecules, and the hydroformylation, the polymerization, and the oxidation of olefins. Homogeneous catalysts are generally more selective, and function under less rigorous conditions than heterogeneous catalysts. Many homogeneous transition metal complexes have their effectiveness reduced by the fact that they undergo undesirable side reactions, such as dimerization. To eliminate this problem, to enhance catalyst selectivity, and to facilitate catalyst-product separation a few experimenters have attached catalytic metal complexes to solid supports, particularly to polymeric supports.

Most workers have used complexes in which phosphine groups are used to link the metal to the solid support. Two types of polymer support, modified polystyrene and silica, have been studied. With polystyrene the form of the polymer can be changed by changing the amount of cross-linking, a feature that appears to have important consequences on the type of catalyst produced. This is the type of support that has been most widely used.

Several useful catalysts have been created from solid-supported metal complexes such as the catalyzed hydrogenation of olefins with polymerically supported palladium (II) and platinum (II) complexes. Catalytic reduction of olefins was also achieved by using polymer-supported tris(triphenylphosphine) chlororhodium (I). Autoclave hydroformylation of cyclohexene was performed by polymer-bound dicobalthexacarbonyl, and ethyl propionate was polymerized into aromatic compounds using $Ni(CO)_2(PPh_3)_2$ as a polymer-attached species. Titanocene dichloride was considerably enhanced in its catalytic ability by attachment to polystyrene polymers. Dimerization of the titanocene was effectively prohibited by isolation of the reactive sites on the polymeric support.

However, all of these systems rely on thermal activation of the catalysts and the olefin reactions are usually conducted at high temperature and pressure. Furthermore, many of the metal-polymer complexes are unstable, the metal gradually detaching from the polymer and entering the solution, making it commercially unfeasible to utilize expensive metals such as rhodium as a catalyst component.

Homogeneous phase reactions under photochemical conditions also have been observed. The disadvantages are the same as experienced with thermal homogeneous phase catalysis and additionally, aggregation or chelation effects are observed forming catalytically inactive compounds and the aggregates sometimes absorb in the same region at higher intensity terminating the reaction due to the internal filter effect.

SUMMARY OF THE INVENTION

A new class of catalysts has been developed in accordance with this invention. The catalyst is synthesized by a photochemical reaction between a low valent transition metal compound and a polymer having potential ligands within or pendant to the polymer backbone. Photochemically generated transition metal species are immobilized on the polymer surface and are prevented from losing their activity through dimerization or reaction with impurities. These polymer bound transition metal species may then act as catalysts for a wide variety of industrially important reactions e.g., hydrogenation, isomerization, hydroformylation, carbonylation, etc. These anchored catalysts show linear photocatalytic activity and good stability. Photochemical generation of catalysts also eliminates the use of high temperatures which are normally needed to generate the catalyst thermally.

Other advantages of the new catalyst are: (a) it can operate at room temperature and atmospheric pressure, (b) it remains active for a long period of time, (c) it is easily separable from products.

These and many other objects and many attendant advantages of the invention will become apparent as the invention becomes better understood by reference to the following detailed description when considered in conjunction with the accompanying drawing.

BRIEF DESCRIPTION OF THE DRAWING

The FIGURE is a series of graphs comparing hydrogenation of 0.3 M cyclohexene in benzene by $Fe(CO)_5$, $Fe(CO)_4P\phi_3$, $Fe(CO)_3(P\phi_3)_2$ and iron carbonyl-polymer beads.

DESCRIPTION OF THE PREFERRED EMBODIMENTS

The low valent transition metal compounds are compounds of metals of Groups IV, VI, VII, or VIII of the Periodic Table having a valence lower than the maximum valence coordinated to ligand groups such as carbonyl or trisubstituted phosphines such as triphenyl phosphine. Typical metals are cobalt, nickel, iron, platinum, rhodium, palladium, manganese, chromium, titanium, tantalum, and iridium.

The polymer is a solid support containing ligands capable of coordinating with the low valent transition metal such as cyano, isocyano, trisubstituted phosphine, such as $-CH_2CN$, $-CH_2NC$, $-P(Ph)_2$, $-P(Me)_2$, $P(OMe)_2$, $-OC_6H_4P(Ph)_2$ and the like. The ligand is preferably pendant from the polymer backbone. The polymer may be organic or inorganic such as styrene, acrylic, vinylchloride, silica polymers or copolymers. Representative polymers are poly-p-diphenyl phosphinostyrene, phosphinated, cross-linked polystyrene divinylbenzene substituted with —P(Ph)$_2$, —P(Bu)$_2$, P(OMe)$_2$, —CH$_2$(Ph)$_2$, or —CH$_2$CN, phosphinated PVC, phosphinated silica, polymethacrylate with an ester group such as —C$_6$H$_4$P(Ph)$_2$, —O(CH$_2$)$_3$P(Ph)$_2$, —O(CH$_2$)$_2$ or —O(CH$_2$)$_2$CN. Ph is phenyl, Me is methyl and Bu is butyl.

The polymer must be insoluble in the irradiation reaction media and in the olefin reaction media. The polymer support may be in the form of particles, sheets, films, strands, hollow fibers or as a coating on a surface. The polymeric substrate is preferably a high area substrate such as porous particle having a diameter below 100 microns or coated onto a carrier such as glass particles.

The metal is found to be firmly bound to the polymers. The polymer contains at least 0.1% metal, generally from 2 to 20% metal by weight. The invention is applicable to all prior homogeneous phase transition metal coordination compound catalysts. The ligand coordination group can be supplied by the metal compound and/or by the polymeric support. Exemplary metal complex catalysts are provided in the following table:

TABLE I

| | |
|---|---|
| Rh$_4$(CO)$_{12}$ | Rh$_6$(CO)$_{16}$ |
| [RhCl(C$_2$H$_4$)$_2$]$_2$ | [Rh(CO)$_2$Cl]$_2$ |
| RhCl(PPh$_3$)$_3$ | RhCl$_3$ |
| RhCl$_3$ | H$_2$PtCl$_6$ |
| RhCl(PHPh$_2$)$_3$ | Co(CO)$_2$(PPh$_3$)$_2$ |
| K$_2$PdCl$_4$ | RhH(CO)(PPh$_3$)$_3$ |
| Titanocene | Ru$_3$(CO)$_{12}$ |
| RhH(CO)(PPh$_3$)$_3$ | Ru$_3$(CO)$_{10}$(NO)$_2$ |
| Ni(CO)$_4$ | Os$_3$(CO)$_{12}$ |
| Rh$_4$(CO)$_{10}$(PPh$_3$)$_2$ | Mn$_2$(CO)$_{10}$ |
| Fe(CO)$_3$(PPh$_3$)$_2$ | W(CO)$_6$ |
| Cr(CO)$_6$ | Fe(CO)$_4$PPh$_3$ |
| Fe(CO)$_5$ | Ru(CO)$_3$(PPh$_3$)$_2$ |
| Mo(CO)$_5$PPh$_3$ | Cr(CO)$_5$PPh$_3$ |

These light-activated, supported catalysts can be utilized for hydrogenation, hydrosilylation, hydroformylation, acetoxylation, polymerization and oligomerization addition reactions as follows:

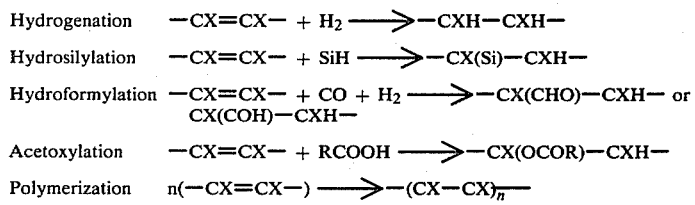

The substrate olefin may be an alkene of the formula R$_1$CH=CH R$_2$ or an alkyne of the formula R$_1$C≡CR$_2$ where R$_1$ and R$_2$ can be aliphatic, aromatic or may be a hydrocarbon or heretocarbon such as ether, ester, acid or the like or R$^1$ R$^2$ groups may be joined to form a cyclic compound. The substrate olefin may be a short chain compound having less than 20 carbon atoms or may be of polymeric length. Representative olefin substrates are provided in the following table:

TABLE II

| ALKENE | CYCLOALKENE | ARENE | ALKYNE |
|---|---|---|---|
| ethylene | cyclohexene | benzene | acetylene |
| propylene | Δ$^2$ cholestene | napthalene | hex-2-yne |
| but-1-ene | cyclooctene | styrene | phenyl-acetylene |
| hex-1-ene | cyclododecene | anthracene | acetylene |
| pent-1-ene | cycloocta-1,3-diene | | |
| vinyl acetate | | | |
| Styrene | | | |
| isoprene | | | |
| butadiene | | | |
| soybean methyl ester | | | |
| trans-pent-2-ene | | | |
| vinyl ethyl ether | | | |
| isobutene | | | |

POLYSTYRENE BEADS

Polystyrene beads of varying degrees of crosslinking were utilized. Eastman polystyrene—2% divinylbenzene copolymer beads, Dow polystyrene XFS-4022—20% divinylbenzene copolymer beads, Rohm and Haas XE-305 macroreticular polystyrene beads, and Bio. Rad. S-X1 chloromethylated 200–400 mesh polystyrene beads were the starting materials for preparation of phosphorylated polymeric supports.

CHLOROMETHYLATION OF BEADS

The polystyrene beads were chloromethylated by the method of Pepper, Paisley, and Young, J. Chem. Soc., 4097 (1953) which reacts chloromethylethyl ether and polystyrene in the presence of SnCl$_4$. The polymer was washed after the reaction with various rinses of aqueous, acidic, and pure dioxane, followed by further washing with methanol. The chloromethylated polymer is then vacuum dried for a day or two.

PHOSPHORYLATION OF CHLOROMETHYLATED POLYSTYRENE

Lithiodiphenylphosphine was prepared from diphenylphosphine and lithium according to the method of Tamborski, J. Org. Chem. 27, 619(1962). The details of the reagent's preparation and subsequent addition to polymer were those provided by Grubbs et al; J. Macromol Sci-Chem., A7(5), 1047 (1973). Preparations of polystyrene beads containing excess Li$^+$PPh$_2^-$ were hydrolyzed with wet acetone and were then washed following Evans and Pittman's directions, J. Organometal Chem., 67, 295 (1974). After repeated washing of the phosphorylated polystyrene, the beads were vacuum dried for several days.

ADDITION OF METAL COMPLEXES TO PHOSPHORYLATED POLYMERS

In general, metal coordination complexes such as Cr(CO)$_6$, Fe(CO)$_5$ were added by photolyzing the metal coordination complex in THF and then adding the polymer and stirring in the dark. Direct photolysis of the metal coordination complex and polymer in THF sometimes gave undesirable side reactions. When beads and metal complex were photolyzed together, it was critical that the mixture not be over irradiated since multiple attachment of polymer phosphines to one metal center increased rapidly beyond a certain point in irradiation.

After attachment of the catalyst to the bead phosphines, the polymer was washed extensively with solvent such as THF and benzene. Then the beads were very thoroughly dried under vacuum. The final product had its IR spectrum measured by examining a pellet of crushed polymer and KBr. Comparison of the carbonyl region to the spectra of the analogous phosphinated complexes allowed elucidation of the species present on the polymer and determination of their relative concentrations.

PHOTOHYDROGENATION AND ISOMERIZATION USING POLYMER-ATTACHED METAL COMPLEXES

These experiments were run under a constant atmosphere of solvent saturated $H_2$. The polymer supported metal complex was put in a pyrex test tube with a sidearm regulated by a stopcock. The solvent, olefin, and a stirring bar were added, and after argonation or freeze-thaw degassing the tube, which was closed with a rubber serum cap, was attached through the sidearm to a line of solvent saturated $H_2$ which was also connected to a bubbler. In this manner the solution was held under a constant pressure of $H_2$, and evaporation of solvent was kept to a minimum. The solution's metal composition could be maintained for at least a day.

The sample tube was then placed in an irradiation train and photolyzed while stirred by the magnetic stirring bar. Periodically aliquots were removed from the solution by inserting a 10 $\mu l$ syringe needle through the rubber serum cap. Formation of hydrogenation or isomerization products during irradiation was monitored by injection of a solution sample into an appropriate gc column.

GAS CHROMATOGRAPH

Samples were examined periodically by gas chromatographing the solution components. A Hewlett-Packard 700 was used, and mixtures were separated by employing UCW-98, SE-30, and $\beta\beta'$ columns.

IRRADIATION OF SAMPLES

Bead solutions were photolyzed with either a 200 W Hg-Xe, a 100 W Gh-Xe, or a 150 W Hg lamp. These sources were filtered by various Corning colored glass filters.

SPECTRAL MEASUREMENTS

Infrared spectra were obtained using KBr pellets or NaCl solution cells on a Perkin-Elmer 225 spectrophotometer. UV-VIS absorption spectra were measured with a Cary 17 spectrophotometer. Emission and excitation spectra were taken using a Perkin-Elmer MPF-3 fluorescence spectrophotometer. A phosphorescence attachment with the chopper removed allowed 77° K. spectra to be obtained.

ATTACHMENT OF CR(CO)$_4$-NORBORNADIENE TO PHOSPHORYLATED BEADS $Cr(CO)_4$-norbornadiene was irradiated in THF with phosphorylated polystyrene and CO was observed given off. The beads were washed and dried before further use.

HYDROGENATION WITH CR(CO)$_3$-NORBORNADIENE (P$\phi_2$CH$_2$-) BEADS

3% hydrogenation of norbornadiene ($10^{-1}$ M solution) was observed when the beads were irradiated with $H_2$ atmosphere with pyrex filtered light.

CR(CO)$_5$P$\phi_2$CH$_2$-POLYSTYRENE PHOTOHYDROGENATION

This polymer supported complex was used to photohydrogenate norbornadiene. 5% hydrogenation of a $10^{-1}$ M solution of norbornadiene was achieved but predominantly rearrangement to quadricyclene was observed using pyrex filtered light. Synthesis of Fe($CO)_3(P\phi_3)_2$ was achieved by photolyzing $Fe(CO)_5$ and $P\phi_3$ in THF. The THF was removed, and the residue was sublimed at 180° C. The sublimation removed the $P\phi_3$ and $Fe(CO)_4P\phi_3$. $Fe(CO)_3(P\phi_3)_2$, which has not been previously reported to photohydrogenate, was observed to hydrogenate benzene solutions of cyclohexene, cis-cyclooctene, cis-3-hexene, and isoprene. The hydrogenation rates were a little slower than those reported for the same substrates employing $Fe(CO)_5$ as a catalyst. $Fe(CO)_3(P\phi_3)_2$ tends to form a precipitate when irradiated with olefin in the solution and the activity falls off sharply. The amount of precipitate formed and the speed with which it appears in the solution is increased by the use of pyrex filtered light compared to using 366 nm light. Hydrogenation definitely proceeds better at 366 nm. Photoisomerization is also observed and in the case of cis-cyclooctene was quite fast compared to hydrogenation.

FE(CO)$_4$P$\phi_3$ PHOTOHYDROGENATION $Fe(CO)_4P\phi_3$ homogeneous solutions also hydrogenate the same substrates mentioned above, in addition to other substrates such as 1,3-pentadiene. The photohydrogenation rate for $Fe(CO)_4P\phi_3$ is also slower than $Fe(CO)_5$, but activity does not fall off as rapidly as $Fe(CO)_3(P\phi_3)_2$ due to the fact that dilute solutions are relatively stable. Precipitation occurs, but only after prolonged irradiation and not nearly to the degree encountered with $Fe(CO)_3(P\phi_3)_2$. The use of 366 nm light appears to also be more suitable for $Fe(CO)_4P\phi_3$ than the use of pyrex filtered irradiation. Isomerization was also observed upon photolysis, however, the relative isomerization abilities of $Fe(CO)_4P\phi_3$ and $Fe(CO)_3(P\phi_3)_2$ were not compared.

SYNTHESIS OF IRON CARBONYL PHOSPHINATED BEADS

Iron carbonyl groups may be added to phosphorylated polystyrene by either pre-irradiation of dilute $Fe(CO)_5$ THF solutions and subsequent thermal addition of the polymer phosphine groups or by irradiation of beads and $Fe(CO)_5$ together in THF solution. If the $Fe(CO)_5$ is irradiated with the polymer, there is the problem of formation of iron dimers and their incorporation into the polymer. So dilute $Fe(CO)_5$ solutions are necessary, and the irradiation must not be allowed to progress too far. Duration of irradiation will also affect how much disubstituted iron carbonyl is produced.

$Fe(CO)_4(P\phi_3)$ may also be added to beads by irradiation. Both the addition techniques described above are applicable. Infrared measurements of the polymers produced usually show about equal amounts of Fe(-

$CO)_4P\phi_3$ and $Fe(CO_3(P\phi_3)_2$ bead species so that the phosphine group of $Fe(CO)_4P\phi_3$ must be readily exchanged for the polymer phosphine. One advantage of bead complex synthesis with $Fe(CO)_4P\phi_3$ is that the overall reaction is much cleaner because there is essentially no problem with dimer formation. Of course, the disadvantage is that there is always a mixture of iron carbonyl species on the polymer.

PHOTOHYDROGENATION AND ISOMERIZATION WITH IRON CARBONYL PHOSPHORYLATED BEADS

Several experiments were run with phosphorylated beads made from either $Fe(CO)_5$ or $Fe(CO)_4$ $(P\phi_3)$. Photohydrogenation and isomerization were observed with cis-3-hexene using pyrex filtered or Corning 7-54 filtered light. Approximately 10% of a $10^{-1}$ M cis-3-hexene solution was converted to hexane in sixteen hours in a run with 0.3 g of beads present. More than 20% of the hexene isomerized in fifteen hours.

Experiments were run with iron carbonyl beads using cyclohexene because cyclohexene does not isomerize, allowing easier interpretation of the results. These experiments used phosphorylated Bio Rad beads made from $Fe(CO)_5$. Over 50% of a 0.3 M cyclohexene solution was hydrogenated in two days.

ADDITION OF OLEFINS TO $FE(CO)_4P\phi_3$ AND IRON CARBONYL BEADS

It was noted in photohydrogenation of cyclohexene with $Fe(CO)_4P\phi_2CH_2$-polystyrene beads that initial photolysis with ultraviolet light caused a color change of the yellow beads to yellow green. Photohydrogenation did not seem to progress very well with uv-transmitting, visible absorbing filters in the lamp beam. If the glass filter was exchanged for a Corning 7-59 filter transmitting from $\approx 300$ to 500 nm, then hydrogenation proceeds quite well and the beads appeared to become less yellow green. It is believed that an iron carbonyl olefin complex is formed by ultraviolet irradiation and that this complex has considerable absorbance in the visible and can be exposed to visible light to produce hydrogenation of substrate.

Many $Fe(CO)_4$-olefin complexes are known and several conjugated olefin complexes have been isolated. However, only one $Fe(CO)_3(P\phi_3)$ olefin complex has been reported, Angew. Chemie, 13, 534 (1974). To investigate the mechanism of photohydrogenation on the bead surface, attempts were made to examine the iron carbonyl beads once they had on them a reasonable amount of what is presumed to be an olefin complex. Infrared measurements of beads produced by 366 nm irradiation with cis-3-hexene in benzene solution under Ar showed a strong new band at $\approx 2010$ cm$^{-1}$. A similar band appeared when $Fe(CO)_4P\phi_3$ was irradiated in the same manner with cis-3-hexene. It is reasonable to assume that cis-3-hexene did add to the iron complex on the polystyrene to give $Fe(CO)_3(cis-3-hexene)P\phi_2CH_2$-polystyrene.

Making other olefin bead complexes was desirable, but since the presence of the olefin complex would be ascertained with infrared spectroscopy, preparation of several Fe(CO) $(P\phi_3)$ olefin complexes was attempted to determine which of these would be easiest to detect in the presence of bands from $Fe(CO)_4P\phi_2CH_2$-polystyrene and $Fe(CO)_3(P\phi_2CH_2—)_2$. Some of the complexes which were made are described below.

REACTION OF $FE(CO)_4P\phi_3$ AND MALEIC ANHYDRIDE $Fe(CO)_4$ $P\phi_3$ and maleic anhydride were photolyzed with 366 nm light in benzene. After a couple of hours of irradiation the solution was turbid, and an infrared spectrum was taken of the reaction mixture. Small new peaks at 2000 cm$^{-1}$ and 1870 cm$^{-1}$ were found. A dark yellow brown precipitate formed after further irradiation and was filtered out and put in KBr to make a pellet for an IR measurement. There was very little of anything in the carbonyl region and that appeared to be $Fe(CO)_4P\phi_3$. The precipitate is perhaps an organic polymer substance produced from maleic anhydride.

T-CINNAMIC ACID ADDITION TO $FE(CO)_4PO_3$

Irradiation of $Fe(CO)_4P\phi_3$ and t-cinnamic acid in benzene under Ar gave a reaction mixture which had in addition to $Fe(CO)_4P\phi_3$ peaks, a relatively strong $\approx 1890$ cm$^{-1}$ band. Higher frequency bands may have been masked by $Fe(CO)_4P\phi_3$. The new absorption is not $Fe(CO)_4$ olefin since 1890 cm$^{-1}$ is not part of its infrared spectrum.

FORMATION OF $FE(CO)_4(P\phi_3)(CYCLOHEXENE)$ $Fe(CO)_4P\phi_3$ was photolyzed with cyclohexene in benzene solution with 366 nm light for 16 hours. small new peaks were observed at 2100 cm$^{-1}$ and 1890 cm$^{-1}$.

OTHER ATTEMPTS TO MAKE $FE(CO)_2(P\phi_3)$ (OLEFIN) COMPLEXES

Methacrylic acid was irradiated with $Fe(CO)_4(P\phi_3)$ and a small peak at $\approx 2100$ cm$^{-1}$ was found. t-2-pentene and 2-methyl-2-butene did not seem to form significant amounts of the olefin complex, at least not under the conditions used.

ISOLATION OF $FE(CO)_3(P\phi_3)(OLEFIN)$ COMPLEXES

Several of the reaction mixtures which produced $Fe(CO)_3(P\phi_3)(olefin)$ complexes were rotoevaporated in the hope of obtaining a residue from which the olefin complex could be isolated but in no case was this possible. The olefin complexes always seemed to fall apart when completely dried. It is very likely that these complexes are too labile to be readily removed from a stabilizing olefin solution. It is quite likely that they can be isolated at low temperatures.

REACTION OF ACRYLONITRILE WITH $FE(CO)_4PO_3$ AND WITH $FE(CO)_4(P\phi_2CH_2$-POLYSTYRENE) BEADS Acrylonitrile, which has a free C≡N peak at $\approx 2230$ cm$^{-1}$, was photolyzed with $Fe(CO)_4P\phi_3$ (bands at 2055, 1978, and 1943 cm$^{-1}$) in benzene to give a solution with a small peak at 2280 cm$^{-1}$, a large peak at 2240 cm$^{-1}$, and other bands at 2050, 2020, 1970, and 1940 cm$^{-1}$. When phosphorylated beads with attached iron carbonyl were irradiated with acrylonitrile in benzene, beads were produced which after thorough washing and drying and incorporation into a KBr pellet were observed to have IR peaks at 2180 cm$^{-1}$ and 1940 cm$^{-1}$. The $\approx 2040$ and 1970 cm$^{-1}$ peaks usually seen with $Fe(CO)_4$ attached to polystyrene phosphines were absent. It seemed very obvious that $Fe(CO)_3(acrylonitrile)(P\phi_2CH_2$-polystyrene) was produced and was quite stable considering that it was washed and vacuum dried and made into a KBr pellet. Attempts to isolate the non-bead acrylonitrile complex failed completely due to disintegration of the complex upon evaporation of olefin and solvent.

ADDITION OF $Co_2(CO)_8$ TO PHOSPHORYLATED POLYSTYRENE $Co_2(CO)_8$ was photolyzed in the presence of phosphorylated beads, olefin, and $H_2/CO$ in benzene and traces of aldehydes were observed.

A number of different degrees of phosphorylation were created in the phosphorylated polymers. Generally one benzene ring out of ten had a phosphine residue, but polymers that had as many as 40% of the rings phosphorylated were produced. Many different experiments were run with polymers. In general, it appeared that one out of ten or slightly greater ratios worked best. In the case of higher ratios the metal complexes were generally chelated so that the potential production of highpercentage metal polymers was not realized.

A definite advantage of the polymer-attached metal complexes examined was the linearity of their photocatalytic rates. The data given in the FIGURE were collected with the parameters specified below.

(a) All samples had 0.3 M cyclohexene in benzene. There was 20 ml of solution in each tube.
(b) All irradiations were performed in quartz tubes with 500 ml reservoirs containing hydrogen at a pressure of 25 inches.
(c) The irradiations were performed with a 1000 W lamp with a Corning 7-59 filter ($\approx$300 to 500 nm).
(d) The homogeneous iron complexes were $3\times10^{-3}$M. The bead sample had 0.3 g of the beads. This set of beads had $\approx$4% Fe attached.
(e) All experiments were conducted at room temperature and the reactions were continuously stirred.

The FIGURE shows the production of cyclohexane using $Fe(CO)_5$, $Fe(CO)_4P\phi_3$, $Fe(CO)_3(P\phi_3)_2$, and polymer attached iron carbonyl as catalysts. All of the homogeneous solution catalysts fall off from their initial hydrogenation rates after a few hours and all of them form precipitates, $Fe(CO)_3(P\phi_3)_2$ especially. The bead supported catalyst hydrogenates with a linear rate and does not appreciably deteriorate in the time range indicated.

The reason for increased linearity of hydrogenation probably arises from the fact that catalyst destroying pathways, such as those that cause the homogeneous solutions to precipitate, are avoided by separation of the metal centers on the polymer. The polymer catalyst is also probably stabilized by the fact that metal centers which are photolyzed off the surface are recaptured very quickly before they can diffuse from the polymeric matrix. Experiments in which iron carbonyl phosphorylated polymers were photolyzed in a solution with cis-1,2 bis-diphenylphosphinoethylene present did not produce significant amounts of free iron carbonyl chelates in the solution as would be expected if appreciable amounts of iron carbonyls diffused in and out of the polymer during irradiation.

It is to be realized that only preferred embodiments of the invention have been described and that numerous substitutions, modifications and alterations are permissible without departing from the spirit and scope of the invention as defined in the following claims.

What is claimed is:

1. A method of preparing an olefin addition catalyst comprising the steps of:
    forming a solution of a low valent transition metal coordination compound in organic solvent;
    irradiating the solution with ultraviolet radiation to form photochemically generated transition metal species;
    combining an insoluble organic polymeric support having ligands for said metal with said species; and
    attaching said photochemically generated species to said ligands in an amount of at least 0.1% by weight of metal on said polymeric support.

2. A method according to claim 1 in which the wavelength of the radiation is from 300 to 500 nm.

3. A method according to claim 1 in which the metal content of the catalyst is from 2 to 20% by weight.

4. A method according to claim 1 in which the solution is irradiated to form the species before addition of the support.

5. A method according to claim 1 in which irradiation is discontinued before a plurality of polymeric ligands attach to a single metal atom.

* * * * *